(12) United States Patent
Bartie et al.

(10) Patent No.: US 6,210,325 B1
(45) Date of Patent: Apr. 3, 2001

(54) CAM-ACTIVATED ADJUSTABLE ARM AND ILLUMINATED TUBULAR RETRACTOR

(75) Inventors: Bruce Bartie, Stillwater; Todd W. Sharratt, Cottage Grove; Steven M. LeVahn, St. Paul, all of MN (US)

(73) Assignee: Minnesota Scientific, Inc., New Brighton, MN (US)

( * ) Notice: Subject to any disclaimer, the term of this patent is extended or adjusted under 35 U.S.C. 154(b) by 0 days.

(21) Appl. No.: 09/409,294

(22) Filed: Sep. 29, 1999

Related U.S. Application Data
(60) Provisional application No. 60/102,788, filed on Oct. 2, 1998.

(51) Int. Cl.[7] .................................................. A61B 1/32
(52) U.S. Cl. ........................... 600/229; 600/184; 600/245
(58) Field of Search .................................... 600/184, 201, 600/205, 208, 227, 228, 229, 245

(56) References Cited

U.S. PATENT DOCUMENTS

| | | |
|---|---|---|
| 2,893,278 | 7/1959 | Cooper . |
| 3,858,578 | 1/1975 | Milo . |
| 4,143,652 | 3/1979 | Meier et al. . |
| 5,400,772 | 3/1995 | LeVahn et al. . |
| 5,513,827 | * 5/1996 | Michelson . |
| 5,792,044 | * 8/1998 | Foley et al. ........................... 600/114 |
| 5,865,730 | * 2/1999 | Fox et al. .......................... 600/229 X |
| 5,947,896 | * 9/1999 | Sherts et al. ........................... 600/229 |
| 5,967,970 | * 10/1999 | Cowan et al. ......................... 600/207 |
| 5,967,972 | * 10/1999 | Santilli et al. .................... 600/229 X |

* cited by examiner

Primary Examiner—Jeffrey A. Smith
(74) Attorney, Agent, or Firm—Kinney & Lange, P.A.

(57) ABSTRACT

A retractor system of the present invention includes an adjustable arm, a carriage, and an activating device disposed in the carriage. The activating device causes movement of at least the adjustable arm to selectively stiffen or release the adjustable arm. The activating device further includes an engagement mechanism that causes movement of at least the carriage to selectively move the carriage. The present invention further includes a tubular retractor distally attached to the adjustable arm having a fiber optic cable embedded in the case of the tubular retractor that is capable of lighting the distal end of the tubular retractor when connected to a light source.

28 Claims, 4 Drawing Sheets

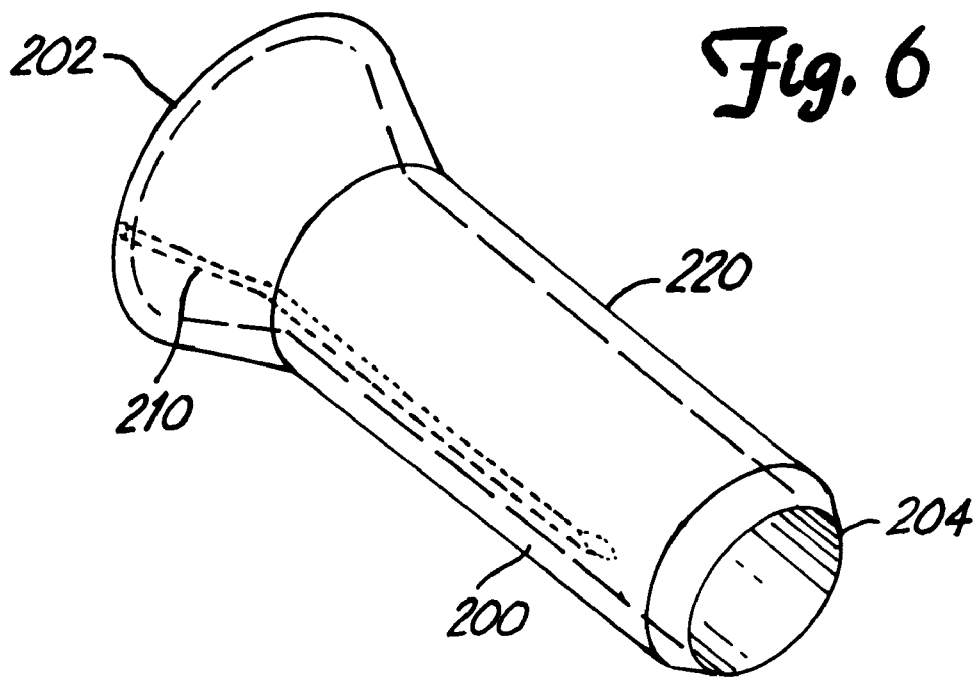
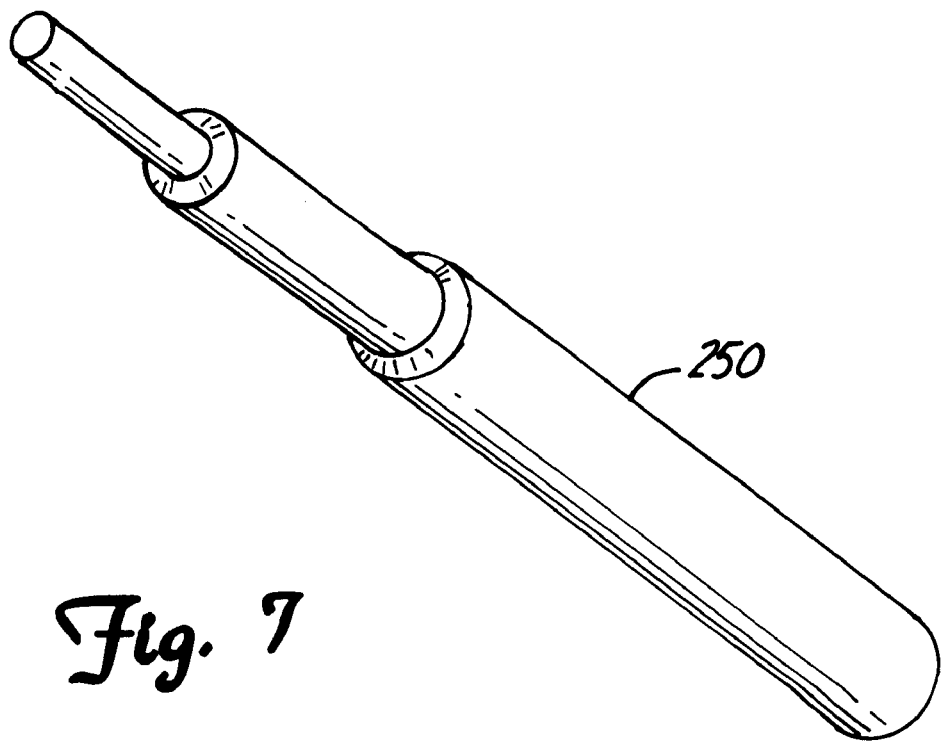

CAM-ACTIVATED ADJUSTABLE ARM AND ILLUMINATED TUBULAR RETRACTOR

This application claims benefit of Provisional Appl. No. 60/102,788, filed Oct. 2, 1998.

BACKGROUND OF THE INVENTION

The present invention generally relates to a retractor system that is useful in surgical procedures. More specifically, the present invention relates to a surgical support structure, such as a retractor apparatus, and to a clamping mechanism for a retractor system. The present invention further relates to illuminating a retractor apparatus.

During many types of surgical procedures, such as micro endoscopic and direct division discectomy, it is customary to use a retractor. The retractor is used to hold back tissue proximate a surgical incision to enable a surgeon to work at and in the surgical incision. Retractors typically include a blade and an arm, such as a shaft, to which the blade is attached. The retractor is generally held in place by attachment to a retractor support apparatus that is positioned over a support surface, such as an operating table. The retractor support is usually attached to a side rail located along one or more sides of the operating table by a clamping device, such as a fulcrum clamp or a cammed clamp.

During surgical procedures, it is highly desirable that the retractor be flexible in order to precisely position the retractor. Quickly securing the retractor in the desired position is also equally important in promoting efficient and safe surgical procedures. Simple horizontal and vertical adjustment of the retractor at the clamping device positioned along the sides of the operating table are also key requirements for successful surgical procedures.

Current retractors are not easy to manipulate and position over the surgical incision since the arm is typically a solid inflexible rod. Locking mechanisms to lock the retractors in a precise location are typically cumbersome and require complex maneuvers that may increase the risk of injury to the patient. Horizontal and vertical adjustment of the retractor at the clamping device that attaches the retractor to the sides of the operating table still remains challenging since the clamping device may be difficult to operate, or be located at a place that may increase the risk of contamination to the patient. Thus, an urgent need presently exists to produce a retractor that overcomes these challenges.

BRIEF SUMMARY OF THE INVENTION

The present invention includes a retractor system having a clamp system that adjustably secures the retractor system to a support surface; and, an adjustable arm including a cam-activated device that selectively stiffens or releases the adjustable arm. The present invention further includes an engagement mechanism of the cam-activated device that causes movement of a carriage in which the engagement mechanism, and thus, the cam-activated device is disposed. The present invention further includes illuminating the retractor apparatus with a fiber optic cable embedded in a light carrying case surrounding a tubular retractor distally attached to the adjustable arm.

BRIEF DESCRIPTION OF THE DRAWINGS

FIG. 6 is a schematic view of a tubular retractor having a fiber optic cable that can be used in the present invention.

FIG. 7 is a schematic view of a dilator that can be used in the present invention.

DETAILED DESCRIPTION

Figure 1:
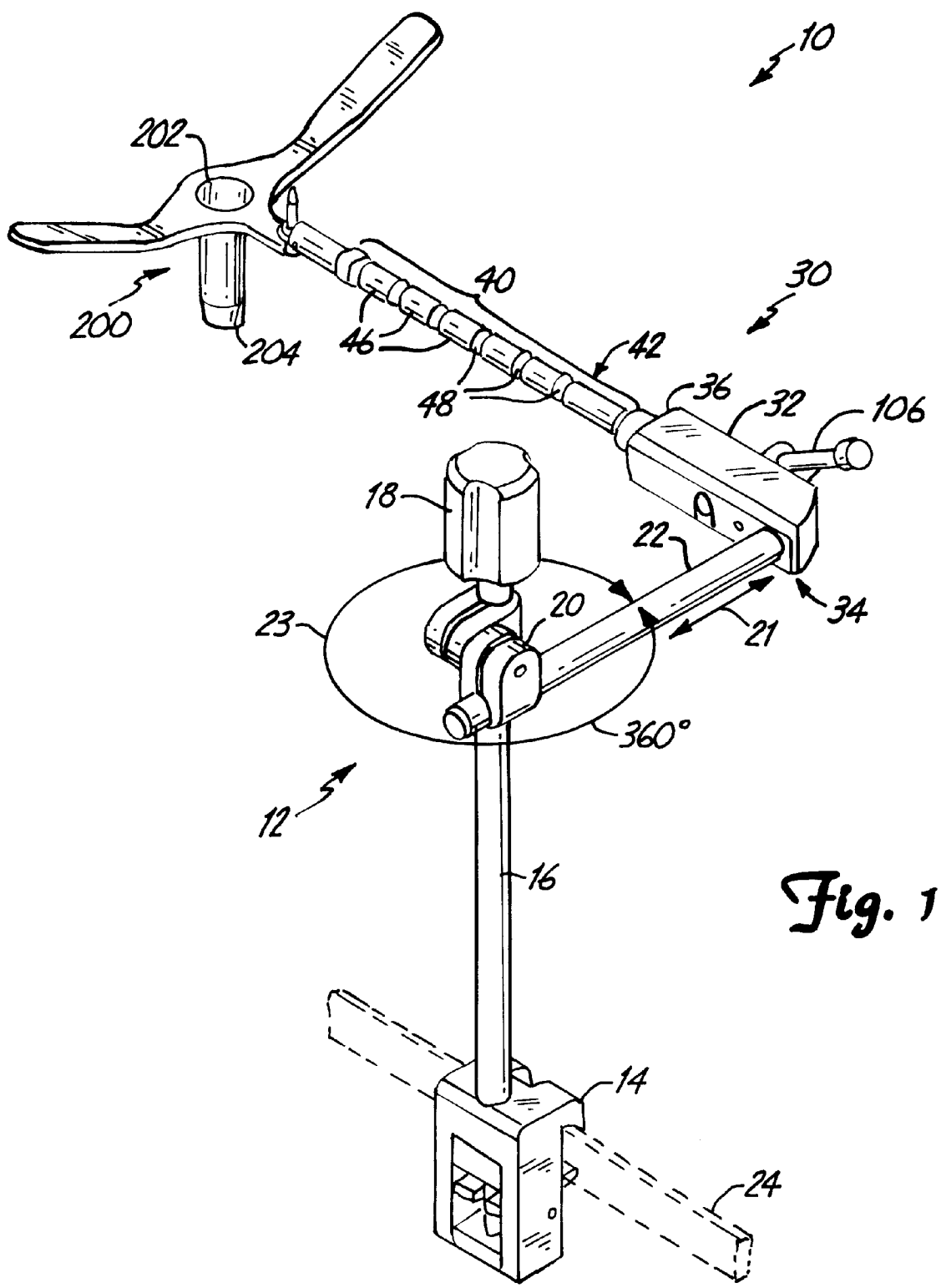
FIG. 1 is a perspective view of a surgical retractor apparatus of the present invention.

A retractor system of the present invention is generally depicted at 10 in FIG. 1. The retractor system 10 includes a clamping system 12 and a retractor apparatus 30. The clamping system 12 includes a support clamp 14, a clamp support rod 16, a clamp knob 18, a retractor clamp 20, and a retractor support rod 22. A suitable clamping system 12, assigned to the same assignee as the present invention, is described in U.S. Pat. No. 5,400,772 and incorporated herein by reference. The clamping system 12 adjustably secures the retractor apparatus 30 to the clamp support rod 16 through retractor clamp 20, as best depicted in FIG. 1. The support clamp 14 clamps to a support surface, such as a rail 24 of an operating table (not shown). Turning the clamp knob 18 releases the support clamp 14 and allows the clamping system 12 to move in a horizontal direction along the rail 24. Vertical adjustment of the clamping system 12 is accomplished by releasing the retractor clamp 20 and sliding the retractor clamp 20 adjustably secured to the retractor support rod 22 to a different vertical position. Horizontal adjustment of the retractor apparatus 30 occurs by releasing the retractor clamp 20 secured to the retractor support rod 22 and moving the retractor support rod 22 in direction 21 if desired. Releasing the retractor clamp 20 also permits the retractor apparatus 30 to freely rotate 360° if desired, as indicated by arrow 23.

The retractor apparatus 30 includes a cam-activated device 32, and an adjustable arm 40, as illustrated in FIG. 1. The cam-activated device 32 locks the adjustable arm 40 in a selected position. The cam-activated device 32 has a clamp support portion 34 and a distal end 36 as best depicted in FIG. 1. The clamp support portion 34 has an aperture (not shown) to receive the retractor support rod 22 to attach the clamping system 12 to the retractor apparatus 30. The distal end 36 receives a proximal end 42 of the adjustable arm 40.

Figure 2:
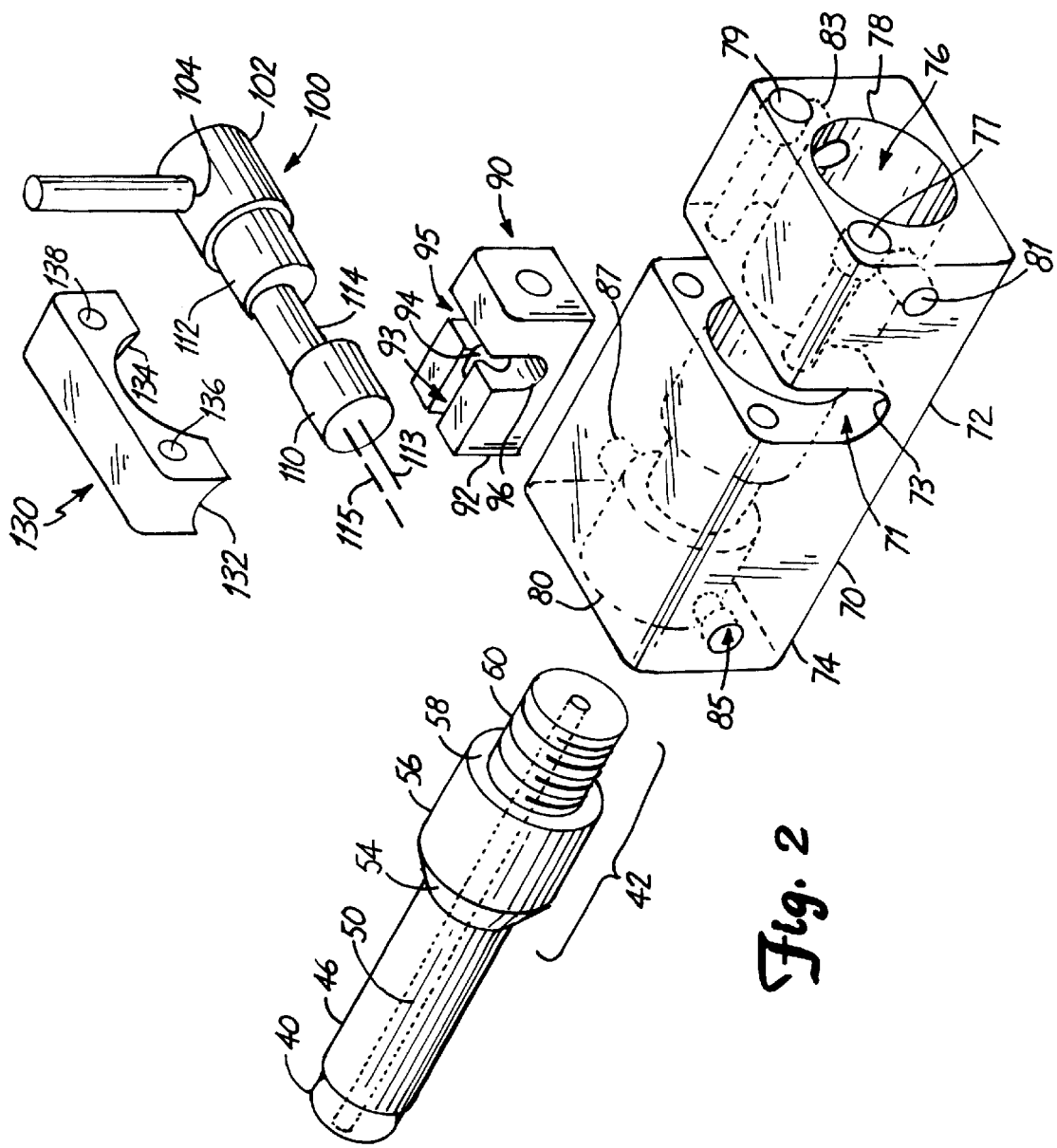
FIG. 2 is an exploded view of an adjustable arm and a cam-activated device of the present invention.
Figure 3:
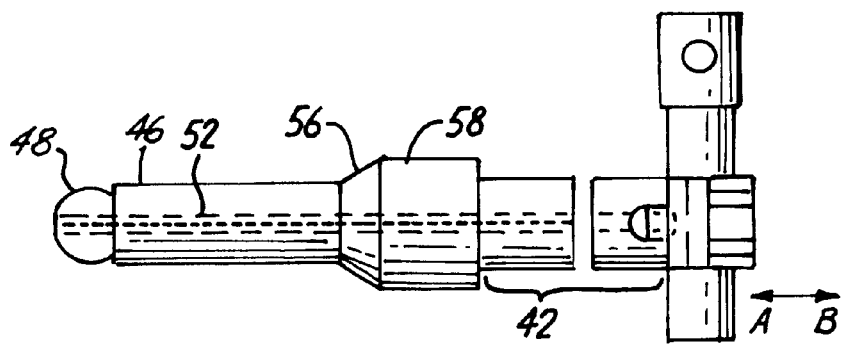
FIG. 3 is a top plan view of the adjustable arm and cam-activated locking device depicted in FIG. 2.
Figure 5:
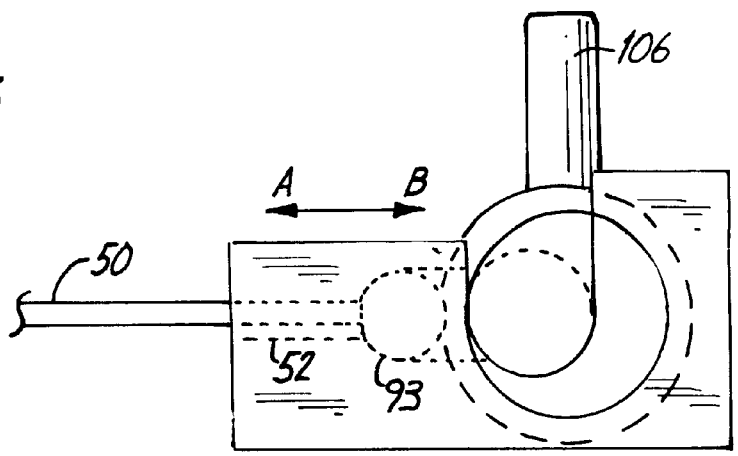
FIG. 5 is a side plan view of the cam-activated locking device depicted in FIG. 3.

The adjustable arm 40, as illustrated in FIGS. 1 and 2, is constructed of alternating cylinder(s) 46 and adjacent sphere (s) 48, connected to each other by a cable 50 extending centrally therethrough. The cable 50 is housed in a bore 52 that extends through each cylinder 46 and adjacent sphere 48 as depicted in FIGS. 3 and 5. The alternating cylinder(s) 46 and adjacent sphere(s) 48 form the adjustable arm 40 that is highly flexible and is easy to manipulate in any direction by the surgeon. Preferably, each cylinder 46 and adjacent sphere 48 are integral with each other being machined from a single piece of metal.

Although alternating cylinders 46 and spheres 48 are used to practice the present invention, any pieced shape may be used to construct the adjustable arm 40, such as barrels, buckets, or the like. Other forms of pieced shapes may be chosen based upon the need to impart more or less flexibility to the adjustable arm 40.

The cam-activated device 32, as best depicted in FIG. 2, includes a housing 70, and a bore 76 that extends centrally through the housing 70. The housing 70 has a proximal portion 72 and a distal portion 74. Likewise, the centrally located bore 76 has a proximal end 78 and a distal end 80.

A frustro-conical surface 54 integral to a cylindrical surface 56 extends above an externally threaded portion 60 of the adjustable arm 40 to form an annular shoulder 58. An internally threaded section (not shown) at the distal end 80 of the bore 76 threadably engages the externally threaded portion 60 of the adjustable arm 40 to securely fix the adjustable arm 40 to the housing 70.

The retractor apparatus 30 further includes a carriage 90 that engages a camming structure 100 for causing a camming action. The carriage is disposed within the proximal end 78 of the bore 76 and extends into a slot 71 of the housing 70. The carriage 90 prevents the camming structure 100 from moving when disposed in slot 71.

The carriage 90 has a groove 93 disposed on a distal end 92 for receiving the cable 50. The cable 50 is attached to a spherical ball 98, as illustrated in FIGS. 3 and 5. The spherical ball 98 is fixedly attached to a spherical groove 94 illustrated in FIG. 2. The spherical groove has a surface conforming to the surface of the spherical ball 98. Therefore, the spherical ball 98 attaches the cable 50 to the carriage 90 as best depicted in FIG. 5. The groove 93 is substantially perpendicular to a cam slot 95 that has a lower semi-cylindrical surface 96 that engages the camming structure 100.

The camming structure 100 has a cylindrical handle section 102 that includes a cam handle bore 104 for engaging a cam handle 106, and two cylindrical sections 110 and 112 of equal diameter disposed on an axis 113. The two cylindrical sections 110 and 112 are preferably oriented substantially perpendicular to the cam handle 106 as illustrated in FIG. 2. The cylindrical section 112 is proximate to the cylindrical handle section 102. The cylindrical sections 110 and 112 engages the cam slot 95 and prevents the cam structure 100 from moving independently of the carriage 90. The cylindrical section 112 is proximate to the cylindrical handle section 102.

Figure 4:
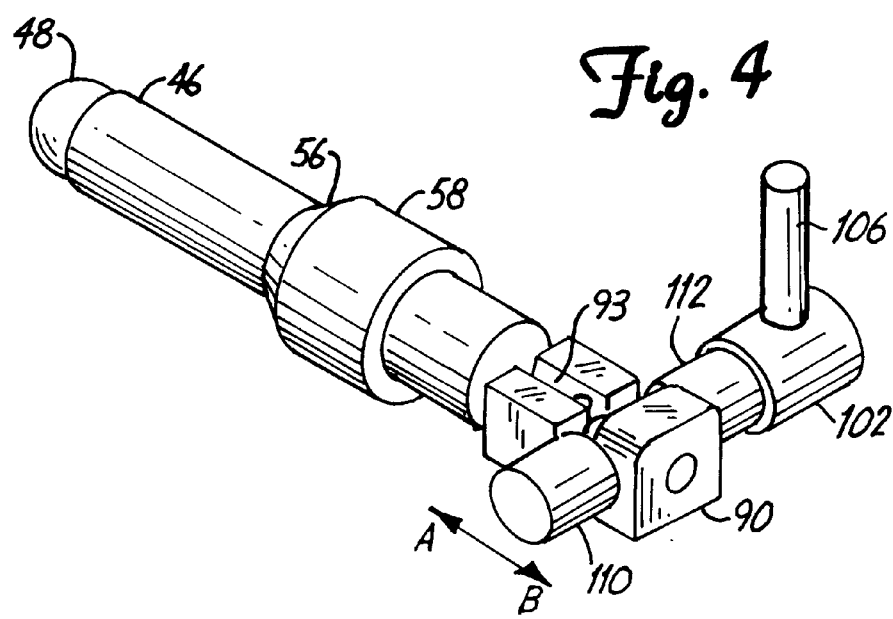
FIG. 4 is a perspective view of the adjustable arm and the cam-activated locking device depicted in FIG. 3.

The camming action is provided by a cam section 114 preferably at an intermediate location between the cylindrical sections 110 and 112. The cam section 114 is smaller in diameter than the cylindrical section 110 and 112. The cam section 114 has a cam axis 115 that is offset from the cylindrical axis 113. When the cam handle 106 on the cylindrical handle section 102 is rotated about the axis 113, the cam section 114 engages the cam slot 95 and thereby moves the carriage 90 in either direction A or in direction B, as best depicted in FIGS. 3, 4, and 5. When the carriage 90 is moved in either direction A or in direction B, the spherical ball 98 attached to the cable 50 is also moved in direction A or in direction B and thereby releases or stiffens the cable 50 in the adjustable arm 40.

The camming structure 100 also engages the slot 71 in the housing 70. The slot 71 has lower semi-cylindrical bottom surfaces 73 and 75 (not shown) that accepts cylindrical sections 110 and 112, respectively.

A cap 130 fits into slot 71 of the housing 70. The cap 130 secures the camming structure 100 in slot 71 while permitting the camming structure 100 to rotate about axis 113. The cap 130 engages cylindrical sections 110 and 112 with arcuate downwardly facing surfaces 132 and 134, respectively. When the cap 130 is positioned within slot 71, apertures 136 and 138 are aligned with apertures 77 and 79, respectively. Cap screws (not shown) are inserted into apertures 77 and 79 and extend into apertures 136 and 138 of the cap 130. The cap 130 also prevents the camming structure 100 from moving upward and downward when disposed in slot 71.

The housing 70 further includes coaxially disposed apertures 81, 83, 85 and 87. Apertures 81 and 83 are located at the proximal portion 72 of the housing 70. Apertures 85 and 87 are positioned at the distal portion 74 of the housing 70. Apertures 81 and 85 are internally threaded (not shown) to accept set screws (not shown) that extend into the apertures 83 and 87 past the bore 76. The set screws (not shown) that are threadably inserted into apertures 81, 83, 85 and 87 may be used to engage a mounting rail (not shown) to secure the retractor apparatus 30 to a support surface (not shown).

Set screws (not shown) that are threadably inserted into apertures 85 and 87 engage the externally threaded portion 60 of the adjustable arm 40. The externally threaded portion 60 may be turned to decrease or increase the tension in the cable 50 with respect to the carriage 90. This feature is important since the appropriate tension in the cable 50 must be maintained so that when the carriage 90 is moved in direction A or in direction B, the cylinders 46 and adjacent spheres 48 are selectively placed in a relaxed or locked position. The set screws (not shown) that are threadably inserted into apertures 85 and 87 engage the externally threaded portion 60 to lock the externally threaded portion 60 in a selected position in the housing 70 and at a selected distance from the carriage 90.

In a preferred embodiment (not shown), a microscope is adjustably secured above the proximal end 202 of the tubular retractor 200 for use in surgical procedures, such as direct vision or micro endoscopic discectomy. The microscope has a light fixedly attached to the microscope for viewing a surgical incision under the microscope. The tubular retractor 200 with the microscope is positioned over the surgical incision and the light of the microscope illuminates the surgical incision by transmission of light through the distal end 204 of the tubular retractor 200. Furthermore, the light from the microscope is transmitted along the entire circumference of the distal end 204 of the tubular retractor 200 and illuminates, without shadow formation, an entire portion of the surgical incision.

In another embodiment, the present invention further includes the use of a fiber optic cable 210 that carries light (not shown) from a source (not shown) and transmits the light to a distal end 204 of a tubular retractor 200 as illustrated in FIG. 6. In the prior art, the fiber optic cable 210 was positioned within the tubular retractor 200. The transmission of the light into the tubular retractor 200 provided light from a single point. When instrumentation was inserted into the tubular retractor 200 shadows would develop on a side of the instrument opposite of the light to distort the view for the surgeon.

The present embodiment eliminates this problem since the fiber optic cable 210 is positioned within a light carrying case 220 encasing the tubular, retractor 200. The fiber optic cable 210 is positioned at least about one-half inch from the distal end 204. When the fiber optic cable 210 is connected to a light source (not shown), light is transmitted through the light carrying case 220 through the distal end 204 and emitted along the entire circumference of the distal end 204. Emission of light along the entire circumference of the distal end 204 eliminates shadows developing on any side of the instrument placed in the tubular retractor 200. Eliminating the fiber optic cable 210 from within the tubular retractor 200 also maximizes working area for any instruments that are placed within the tubular retractor 200.

By selectively extending the dilator 250 into the incision site, more precise positioning of the tubular retractor 200 can occur.

A set of dilators is used to separate muscle tissue and localize a site for the introduction of dilator retractor.

All though the present invention has been described with reference to preferred embodiments workers skilled in the art would recognize that changes maybe made in form and detail without departing from the spirit and scope of the invention.

What is claimed is:

1. A retractor system, the retractor system comprising:
   an adjustable arm;
   a carriage;
   an activating device disposed in the carriage;
   the activating device capable of causing movement of at least the adjustable arm to selectively stiffen or release the adjustable arm;
   the activating device further comprising an engagement mechanism, the engagement mechanism capable of causing movement of at least the carriage to selectively move the carriage;
   the engagement mechanism further comprising a camming structure and an engagement member, the camming structure capable of forcing the engagement member into engagement with the carriage;
   a tubular retractor distally attached to the adjustable arm; and
   a clamping device for adjustably securing the retractor apparatus.

2. The retractor system of claim 1 wherein the adjustable arm includes alternating balls and cylinders connected to each other by a cable extending centrally therethrough.

3. The retractor system of claim 2 wherein the engagement member is disposed in the carriage and is attached to the central cable of the adjustable arm.

4. The retractor system of claim 2 wherein the camming structure is disposed to contact the engagement member for forcing the engagement member into engagement with the cable.

5. The retractor system of claim 2 wherein moving the carriage moves at least the cable to decrease or increase the tension in the cable.

6. The retractor system of claim 1 wherein the camming structure has a cam section secured at both ends to cylindrical sections.

7. The retractor system of claim 6 wherein the cam section has a first axis and the cylindrical sections are disposed along a second axis, the first axis being offset from the second axis.

8. The retractor system of claim 1 further including a cylindrical handle section having an aperture that engages a handle.

9. The retractor system of claim 8 wherein movement of the cylindrical handle section rotates at least the camming structure and thereby engages the engagement member to move the carriage.

10. The retractor system of claim 1 wherein the engagement member is a ball.

11. The retractor system of claim 1 wherein the tubular retractor further includes a dilator.

12. The retractor system of claim 1 wherein the tubular retractor further includes a microscope.

13. The retractor system of claim 1 wherein the tubular retractor further includes a fiberoptic cable capable of providing light.

14. The retractor system of claim 13 wherein the fiber optic cable is at least about one-half inch from the distal end of the tubular retractor.

15. A retractor apparatus, the retractor apparatus comprising:
   an adjustable arm;
   a carriage;
   an activating device disposed in the carriage;
   the activating device capable of causing movement of at least the adjustable arm to selectively stiffen or release the adjustable arm;
   the activating device further comprising an engagement mechanism, the engagement mechanism capable of causing movement of at least the carriage to selectively move the carriage; and
   the engagement mechanism further comprising a camming structure and an engagement member, the camming structure capable of forcing the engagement member into engagement with the carriage.

16. The retractor apparatus of claim 15 wherein the adjustable arm includes alternating balls and cylinders connected to each other by a cable extending centrally therethrough.

17. The retractor apparatus of claim 16 wherein the engagement member is disposed in the carriage and is attached to the central cable of the adjustable arm.

18. The retractor apparatus of claim 16 wherein the camming structure is disposed to contact the engagement member for forcing the engagement member into engagement with the cable.

19. The retractor apparatus of claim 16 wherein moving the carriage moves at least the cable to decrease or increase the tension in the cable.

20. The retractor apparatus of claim 15 wherein the camming structure has a cam section secured at both ends to cylindrical sections.

21. The retractor apparatus of claim 20 wherein the cam section has a first axis and the cylindrical sections are disposed along a second axis, the first axis being offset from the second axis.

22. The retractor apparatus of claim 15 further including a cylindrical handle section having an aperture that engages a handle.

23. The retractor apparatus of claim 22 wherein movement of the cylindrical handle section rotates at least the camming structure and thereby engages the engagement member to move the carriage.

24. The engagement mechanism of claim 15 wherein the engagement member is a ball.

25. The retractor apparatus of claim 15 wherein the tubular retractor further includes a dilator.

26. The retractor apparatus of claim 15 wherein the tubular retractor further includes a microscope.

27. The retractor apparatus of claim 15 wherein the tubular retractor further includes a fiberoptic cable capable of providing light.

28. The retractor apparatus of claim 27 wherein the fiber optic cable is at least about one-half inch from the distal end of the tubular retractor.

* * * * *

UNITED STATES PATENT AND TRADEMARK OFFICE
CERTIFICATE OF CORRECTION

PATENT NO. : 6,210,325 B1
DATED : April 3, 2001
INVENTOR(S) : Bruce Bartie et al.

It is certified that error appears in the above-identified patent and that said Letters Patent is hereby corrected as shown below:

<u>Title page,</u>
References Cited, U.S. PATENT DOCUMENTS,
delete "2,893,278", insert -- 2,893,378 --

Signed and Sealed this

Nineteenth Day of March, 2002

Attest:

JAMES E. ROGAN
*Director of the United States Patent and Trademark Office*

*Attesting Officer*